United States Patent [19] [11] 4,326,092
Neuzil [45] Apr. 20, 1982

[54] PROCESS FOR THE SEPARATION OF META-XYLENE

[75] Inventor: Richard W. Neuzil, Downers Grove, Ill.

[73] Assignee: UOP Inc., Des Plaines, Ill.

[21] Appl. No.: 169,552

[22] Filed: Jul. 17, 1980

[51] Int. Cl.³ .............................................. C07C 7/12
[52] U.S. Cl. .................................................... 585/828
[58] Field of Search ......................................... 585/828

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,114,782 | 12/1963 | Fleck et al. | 585/831 |
| 3,133,126 | 5/1964 | Fleck et al. | 585/831 |
| 3,201,491 | 8/1965 | Stine et al. | 585/821 |
| 3,265,750 | 8/1966 | Peck et al. | 585/825 |
| 3,422,848 | 1/1969 | Liebman et al. | 137/625.15 |
| 3,510,423 | 5/1970 | Neuzil et al. | 208/310 |
| 3,558,732 | 1/1971 | Neuzil | 585/828 |
| 3,668,267 | 6/1972 | Hedge | 585/831 |
| 3,686,342 | 8/1972 | Neuzil | 585/828 |
| 3,706,812 | 12/1972 | deRosset et al. | 585/822 |
| 3,773,846 | 11/1973 | Berger | 585/828 |
| 3,917,734 | 11/1975 | deRosset | 585/828 |
| 3,939,221 | 2/1976 | Pearce | 585/828 |
| 3,997,619 | 12/1976 | Neuzil | 585/828 |

Primary Examiner—Curtis R. Davis
Attorney, Agent, or Firm—James R. Hoatson, Jr.; Louis A. Morris; William H. Page, II

[57] ABSTRACT

An adsorptive separation process for separating meta-xylene from a feed mixture comprising meta-xylene and the other $C_8$ aromatics, which process comprises contacting the feed mixture with an adsorbent comprising type Y zeolite containing sodium at the exchangeable cationic sites and having a silica to alumina mole ratio of from about 4.5 to about 5.0, selectively adsorbing substantially all of the meta-xylene isomers to the substantial exclusion of the remaining $C_8$ aromatics and thereafter recovering high-purity meta-xylene. A desorption step may be used to desorb the adsorbed meta-xylene. The process is carried out preferably in the liquid phase.

11 Claims, No Drawings

{ #4,326,092 }

PROCESS FOR THE SEPARATION OF META-XYLENE

BACKGROUND OF THE INVENTION

1. Field of the Invention

The field of art to which the claimed invention pertains is solid-bed adsorptive separation. More specifically, the claimed invention relates to a process for the separation of meta-xylene from a feed mixture comprising meta-xylene and the other $C_8$ aromatics, which process employs a solid adsorbent which selectively removes the meta-xylene from the feed mixture thereby producing a fluid raffinate stream comprising the remaining $C_8$ aromatics.

2. Description of the Prior Art

Although meta-xylene constitutes about one-half of the total product stream in the current processes for the manufacture of $C_8$ aromatics (ethylbenzene and ortho-, meta- and para-xylene), no practical process for its high purity recovery has yet been developed. The difficult and involved prior art separation techniques for recovery of meta-xylene include distillation to obtain higher than the eutectic concentration of meta-xylene followed by crystallization, selective sulfonation, and selective chlorination. One commercialized process for recovery of meta-xylene involves the formation of a complex of meta-xylene, hydrofluoric acid and boron trifluoride, which complex is then extracted by a liquid-liquid extraction technique and finally decomposed to recover the meta-xylene product.

Meta-xylene has great commercial utility because it is needed in the manufacture of certain insecticides and isophthalic acid. Thus, in view of this utility on the one hand, and the above difficult and involved separation techniques on the other, there has long existed a great but unfulfilled need for a more efficient separation process enabling the recovery of high purity meta-xylene.

It is well-known in the separation art that certain crystalline aluminosilicates can be used to separate hydrocarbon species from mixtures thereof. The separation of normal paraffins from branched chain paraffins for example can be accomplished by using a type A zeolite which has pore openings from about 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat Nos. 3,265,750 and 3,510,423 for example disclose processes in which larger pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes.

Because of the commercial importance of para-xylene, the more well-known and extensively used hydrocarbon isomer separation processes are those for separating para-xylene. Para-xylene is used in the manufacture of terephthalic acid which in turn is subsequently employed in the manufacture of various synthetic fibers such as Dacron, a trade-marked product of the duPont Company. In processes described in U.S. Pat. Nos. 3,558,732 and 3,686,342 for example adsorbents comprising particular zeolites are used to separate para-xylene from feed mixtures comprising para-xylene and at least one other xylene isomer by selectively adsorbing para-xylene over the other xylene isomers. In such processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components.

In the process described in U.S. Pat. No. 3,917,734 ethylbenzene is recovered in high purity from a feed mixture comprising ethylbenzene and xylene isomers. The process basically comprises contacting the feed mixture with an adsorbent comprising calcium exchanged type X or type Y zeolites, selectively adsorbing the xylene isomers, and thereafter recovering ethylbenzene as a raffinate component. The adsorbent employed is thus all-xylene selective rather than para-xylene selective as are the adsorbents used in the para-xylene separation process. The adsorbed xylenes may then be recovered, in one embodiment, by contacting the adsorbent with a desorbent material, preferably comprising toluene, thereby desorbing the xylenes and then withdrawing the desorbed xylenes from the adsorbent. In another embodiment the adsorption and desorption are done continuously in a simulated moving bed countercurrent flow system the operating principles and sequence of which are described in U.S. Pat. No. 2,985,589.

In the process described in U.S. Pat. No. 3,133,126 adsorptive separations of meta-xylene from other isomers of xylene are shown, but in each instance from mixtures containing the meta-xylene and only one other isomers. The process was unable to recover meta-xylene from a mixture of all of the xylene isomers and ethylbenzene.

Thus, in spite of the great need, no adsorptive separation process employing an adsorbent selective for meta-xylene over the other xylene isomers and ethylbenzene has heretofore been discovered. I have made such a discovery. The process of my invention effectively achieves separation of meta-xylene from a mixture of all $C_8$ aromatics.

SUMMARY OF THE INVENTION

It is, accordingly, a broad objective of this invention to provide a process for the separation of high-purity meta-xylene at high recoveries from a feed mixture comprising meta-xylene, ethylbenzene and the other xylene isomers. It is a further objective that the process shall employ a simulated moving adsorbent bed.

In brief summary, the invention is, in one embodiment, a process for separating meta-xylene from a feed mixture comprising the xylene isomers and ethylbenzene which process comprises contacting at adsorption conditions the mixture with an adsorbent comprising a type Y zeolite containing sodium at the exchangeable cationic sites and having a silica to alumina mole ratio of from about 4.5 to about 5.0, selectively adsorbing the meta-xylene isomers to the substantial exclusion of the remaining components of the mixture and thereafter recovering high-purity meta-xylene.

The invention is, in another embodiment, a process for separating meta-xylene from a feed mixture comprising the xylene isomers and ethylbenzene which process employs an adsorbent comprising a type Y zeolite containing sodium at the exchangeable cationic sites and having a silica to alumina mole ratio of from about 4.5 to about 5.0 and which process comprises the steps of: (a) maintaining net fluid flow through a column of said adsorbent in a single direction, which column contains at least three zones having separate operational functions occurring therein and being serially interconnected with the terminal zones of the column connected to provide a continuous connection of said zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into said adsorption zone at adsorption conditions to effect the selective adsorption of the meta-xylene to the substantial exclusion of the remaining components of said mixture by the adsorbent in the adsorption zone and withdrawing a raffinate output stream comprising the remaining components from the adsorption zone; (f) passing a desorbent material having an average boiling point substantially different from that of the feed mixture into said desorption zone at desorption conditions to effect the displacement of the meta-xylene from the adsorbent in the desorption zone; (g) withdrawing an extract output stream comprising the remaining components from the desorption zone; and (h) periodically advancing through the column of adsorbent in a downstream direction with respect to fluid flow in the adsorption zone the feed input stream, a raffinate output stream, desorbent input stream, and extract output stream to effect the shifting of zones through the adsorbent and the production of the extract output and raffinate output streams.

Other embodiments and objects of the present invention encompass details about feed mixtures, adsorbents, desorbents, and operating conditions all of which are hereinafter disclosed in the following discussion of each of these facets of the present invention.

DESCRIPTION OF THE INVENTION

At the outset the definitions of various terms used throughout the specification will be useful in making clear the operation, objects and advantages of the process.

A "feed mixture" is a mixture containing one or more extract components and one or more raffinate components to be separated by the process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process the meta-xylene isomer contained in the feed mixture is the extract component and ethylbenzene, ortho and para-xylene are raffinate components. The term "desorbent material" shall mean generally a material capable of desorbing the extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. In one embodiment of the process the raffinate stream and extract stream will each contain desorbent material and at least a portion of the raffinate stream and preferably at least a portion of the extract stream from the separation process will be passed to separation means, typically fractionators, where at least a portion of desorbent material will be separated from each stream to produce an extract product and a raffinate product respectively. The terms "extract product" and "raffinate product" mean products produced by the process containing, respectively, an extract component and a raffinate component in higher concentrations than those found in the extract stream and the raffinate stream. Although it is possible by the process of this invention to produce a high-purity (98% or greater, expressed as a percent of $C_8$ aromatics present) meta-xylene product at high recoveries (95% or greater) it will be appreciated that an extract component is never completely adsorbed by the adsorbent, nor is a raffinate component completely non-adsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of meta-xylene to that of a less selectively adsorbed feed stream component will be lowest in the raffinate stream, next highest in the feed mixture, and the highest in the extract stream. Likewise, the ratio of the concentration of a less selectively adsorbed component to that of the more selectively adsorbed meta-xylene will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise ethylbenzene and the xylene isomers. Mixtures containing substantial quantities of ethylbenzene and the xylene isomers generally are produced by reforming and isomerization processes, processes which are well-known to the refining and petrochemical arts. In reforming processes, a naphtha feed is contacted with a platinum-halogen-containing catalyst at severities selected to produce an effluent containing $C_8$ aromatic isomers. Generally the reformate is then fractionated to concentrate the $C_8$ aromatic isomers in a $C_8$ fraction which may then be further concentrated by solvent extraction processes. Xylene isomerization processes isomerize at isomerization conditions a xylene mixture which is deficient in one or more isomers to produce an effluent containing approximately equilibrium quantities of the $C_8$ aromatic isomers. The equilibrium compositions of the xylene isomers and ethylbenzene at various temperatures are shown in Table 1 below.

TABLE 1

| Equilibrium $C_8$ Aromatic Compositions* | | | |
|---|---|---|---|
| Temperature, °C. | 327 | 427 | 527 |
| Mole Percent of isomers | | | |
| Ethylbenzene | 6 | 8 | 11 |
| Para-xylene | 22 | 22 | 21 |
| Meta-xylene | 50 | 48 | 45 |
| Ortho-xylene | 22 | 22 | 23 |

*Based on API sources

Feed streams to the process of this invention will contain all three of the xylene isomers in addition to ethylbenzene. $C_8$ reformate fractions and isomerates from xylene isomerization processes containing all of the xylene isomers can be charged as feed streams directly to this process.

Feed streams to this process can also comprise effluent streams from processes which have removed varying amounts of one or more xylene isomers. As one example, at least a portion of the orthoxylene may have been previously removed by fractionation from a feed mixture containing the xylene isomers. Ortho-xylene has a boiling point of about 6° F. higher than that of the nearest other $C_8$ aromatic (meta-xylene) and hence can be removed as a bottoms product from ortho-xylene fractionator towers. Such towers will typically contain about 100 to 105 actual trays and will operate with about a 5–8 to 1 reflux to feed ratio. The concentration of ortho-xylene in the effluent or overhead from this fractionation process which can be used as a feedstream to my process will then be less than the concentrations of either para-xylene or meta-xylene. Alternatively at least a portion of the para-xylene may have been previously removed from a feed mixture containing the xylene isomers by a fractional crystallization process or by a solid-bed selective adsorptive process or by a combination of both. In this situation, the concentration of para-xylene in the effluent which is now charged as a feed stream to my process will be less than the concentrations of either ortho-xylene or meta-xylene. As another alternative, perhaps at least a portion of both ortho- and para-xylene will have been previously removed, by the processes described above, from a feed mixture containing the xylene isomers. The concentration of both ortho-xylene and para-xylene in this feed stream to my process would then each be less than that of meta-xylene.

Feed mixtures may also contain small quantities of non-aromatics such as straight or branched chain paraffins, cycloparaffins, or olefinic materials. However, since separation of meta-xylene from a feed mixture by its selective adsorption on a zeolite adsorbent apparently takes place because of a rather delicate acidity/basicity difference between the other xylene isomers, ethylbenzene and the adsorbent, compared to that between meta-xylene and the adsorbent, it is preferred that these contaminants, especially olefins, be less than about 20 vol. % of the feed mixture passed into the process and more preferably be less than about 10 vol. %, so that this difference is not upset. Another reason for having minimum concentrations of non-aromatics in the feed mixture is that all unadsorbed components will appear in the raffinate stream. Unless these components are later removed from the raffinate stream, the purity of that stream will be decreased.

To separate meta-xylene from a feed mixture containing the xylene isomers and ethylbenzene, the mixture is contacted with the particular adsorbent and the meta-xylene is more selectively adsorbed and retained by the adsorbent while the less selectively adsorbed components of the mixture are removed from the interstitial void spaces between the particles of adsorbent and the surface of the adsorbent. The adsorbent containing the more selectively adsorbed meta-xylene is referred to as a "rich" adsorbent—rich in the more selectively adsorbed meta-xylene. The adsorbent can be contained in one or more chambers where through programmed flow into and out of the chamber separation of the isomers is effected. The adsorbent will preferably be contacted with a desorbent material (hereinafter described in more detail) which is capable of displacing the adsorbed xylene isomer from the adsorbent. Alternatively, the adsorbed xylene isomer could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with a feed mixture and a desorbent material in which case the process will be only semicontinuous. In another embodiment a set of two or more static beds may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. The use of such flow systems is therefore preferred in this process. In a more preferred embodiment this process will employ for each adsorbent a separate simulated moving-bed countercurrent flow system. The operating principles and sequence of operation of one such simulated moving-bed countercurrent flow system are described in U.S. Pat. No. 2,985,589 incorporated herein by reference thereto. In such a system it is the progressive movement of multiple liquid access points down an adsorbent chamber that simulates the upward movement of an adsorbent contained in the chamber. Only four of the access lines are active at any one time; the feed input stream, desorbent inlet stream, raffinate outlet stream, and extract outlet stream access lines. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of this process it is generally necessary that three separate operational zones be present in each simulated moving-bed countercurrent flow system in order for the desired operations to take place although in some instances an optional fourth zone may be used.

To aid in understanding the operation of the zones which are used in a preferred embodiment of this process, the zones may be envisioned as containers of adsorbent each having a top boundary and a bottom boundary the containers being stacked one on top of the other with the first container, zone 1, being on top; the second container, zone 2, being under zone 1; the third container, zone 3, being under zone 2; and an optional fourth container, zone 4, being under zone 3. Fluid flow through the zones can be imagined as being from the bottom boundary of zone 4 upwardly through the stack of zones out of the top boundary of zone 1 and back into the bottom boundary of zone 4 while the flow of adsorbent can be imagined as being countercurrent to the flow of fluid, that is downwardly through the top boundary of zone 1 through the stack of zones, out of the bottom boundary of zone 4 and back into the top boundary of zone 1.

Zone 1 is the adsorption zone and is defined as the adsorbent between a raffinate output stream as the top boundary of the zone and a feed inlet stream as the bottom boundary of the zone. In this zone a feed mixture passes into the zone through the feed input stream, an extract component is adsorbed and a raffinate output stream is withdrawn. Adsorbent may be considered as entering the zone at the raffinate output stream boundary, passing through the zone and passing out of the zone at the feed input stream boundary of the zone. The adsorbent entering this zone at the raffinate output stream contains only the raffinate components and desorbent. As it moves downwardly through the zone and contacts the ascending liquid which is richer in the extract components, the selectivity of the adsorbent for the extract components causes them to be adsorbed. The raffinate components and typically some desorbent material are withdrawn as the raffinate output stream. The adsorbent leaving zone 1 and passing into zone 2 at the feed input stream contains all of the adsorbed species.

Immediately upstream of zone 1 with respect to liquid flow through the stack of zones is zone 2 which is the purification zone. This zone is defined as the adsorbent between the feed inlet stream at the bottom boundary of the zone. The basic operations taking place in zone 2 are the displacement from the non-selective void volume of the adsorbent of any raffinate material carried into zone 2 by the adsorbent that passes through this zone and the desorption of any raffinate material adsorbed within the selective pore volume of the adsorbent or adsorbed on the surfaces of the adsorbent particles. Purification is achieved by passing a portion of extract stream material leaving zone 3 (hereinafter described) into zone 2 at zone 2's upstream boundary, the extract outlet stream, to effect the displacement of raffinate material.

Immediately upstream of zone 2 with respect to liquid flow is zone 3 which is the desorption zone. This zone is defined as the adsorbent between the extract outlet stream at the top boundary of the zone and a desorbent inlet stream at the bottom boundary of the zone. Descending adsorbent containing adsorbed extract components enters the zone at the top of the zone and is contacted with desorbent material which enters the zone at the bottom of the zone through the desorbent input stream. Extract components are desorbed and at least a portion of them pass out in the extract output stream.

In some instances an optional zone 4, referred to as a buffer zone, may be utilized. This zone is defined as the adsorbent located between the desorbent input stream as the top boundary of the zone and the raffinate output stream as the bottom boundary of the zone and when used is located immediately upstream of zone 3. Zone 4 is utilized to reduce the amount of external desorbent material that has to be passed into the desorption zone to desorb the extract components. This is done by passing a portion of the raffinate output from zone 1 into zone 4 to displace desorbent material that is carried out of zone 3 with the adsorbent leaving zone 3 back into zone 3. Zone 4 will contain enough adsorbent so that a raffinate component present in the raffinate output stream passing out of zone 1 and into zone 4 can be prevented from passing into zone 3 thereby contaminating the extract output stream removed from zone 3 and also reducing the yield of the raffinate product. In the instances in which the fourth operational zone is not utilized the portion of the raffinate output stream passing from zone 1 to zone 3 must be carefully monitored in order that the flow of this stream can be stopped when there is an appreciable quantity of a raffinate component present so that the extract output stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,442,848. Both of the aforementioned patents disclose a rotary type connection valve in which the suitable advancement of the various input and output streams from fixed sources can be achieved without difficulty.

In many instances, one operational zone will contain a much larger quantity of an adsorbent than some other operational zone. For instance, in some operations the buffer zone will contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an adsorbent be located in a single column which is divided into zones, and the use of multiple chambers or a series of columns is also within the scope of this embodiment.

It is not necessary that all of the input or output streams be simultaneously used, and in fact, in many instances some of the streams can be shut off while others effect an output of material. One apparatus which can be utilized to effect the process of this invention in a preferred embodiment will contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations function intermittently as a conduit through which material passes into or out of the process.

It is contemplated that at least a portion of the raffinate output streams will be passed into a separation means wherein at least a portion of the desorbent material will be separated at separating conditions to produce a raffinate product containing a reduced concentration of desorbent material and a desorbent stream which can be reused in the process. Preferably, but not necessary to the operation of the process, at least a portion of the extract output stream will also be passed to a separation means wherein at least a portion of the desorbent material will be separated at separating conditions to produce another desorbent stream which can be reused in the process and an extract containing a reduced concentration of desorbent material. The separation means will typically be a fractionation column, the design and operation of which is well-known to the separation art.

Reference can be made to D. B. Broughton U.S. Pat. No. 2,985,589 and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, incorporated herein by reference, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of an extract product than can be obtained with liquid-phase operation over those obtained with vapor-phase operation. Preferred adsorption and desorption conditions will include a temperature within the range of from about 20° C. to about 250° C. and a pressure within the range of from about atmospheric to about 500 psig.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially constant pressures and temperatures to insure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail) it is preferred that the adsorbent be more selective for all of the extract components with respect to a raffinate component that it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component.

Desorbent materials to be used in the process of this invention should additionally be substances which are easily separable from the feed mixture that is passed into the process. After desorbing the extract components of the feed, both desorbent material and the extract components are removed in admixture from the adsorbent. Likewise, the raffinate components are withdrawn from the adsorbent in admixture with desorbent material. Without a method of separating desorbent material, such as distillation, the purity of neither the extract components nor the raffinate component would be very high. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, it was found that desorbent materials comprising mono-aromatic hydrocarbons are particularly effective. Specifically, desorbent material comprising toluene is especially preferred for this type of operation.

With the operation of this process now in mind, one can appreciate that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of extract components with respect to a raffinate component and the desorbent material; and sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below.

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. For optimum performance desorbent materials should have a selectivity equal to about 2 or less than 1 with respect to all extract components so that all of the extract components can be extracted as a class and all raffinate components cleanly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the absorbent; faster rates of exchange reduce the amount of desorbent material needed to remove the extract component and therefore permit a reduction in the operating cost of the process. With faster rates of exchange less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed paraffinic tracer (n-nonane for instance) and of the particular C8 aromatic isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces, adsorbent performance can be rates in terms of capacity index for an extract component, selectivity for one isomer with respect to the other, and the rate of desorption of extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous counter-current liquid-solid contacting device. The general operating principles of such a device have been previously described and are found in Broughton U.S. Pat. No. 2,985,589. A specific pilot plant scale apparatus known as a "carousel unit" utilizing these principles is described in deRosset et al U.S. Pat. No. 3,706,812, incorporated herein by reference. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of C8 Aromatics by Adsorption" by A. J. deRosset, R. W. Neuzil, D. J. Korous, and D. H. Rosback presented at the American Chemical Society, Los Angeles, California, Mar. 28 through Apr. 2, 1971, incorporated herein by reference.

The feasibility of separating meta-xylene from a feed mixture comprising ethylbenzene and the xylene isomers by selective adsorption of the meta-xylene on the particular adsorbent disclosed herein, which was demonstrated by pulse test results, was confirmed by continuous testing in the laboratory-sized apparatus described above.

The adsorbent to be used in the process of this invention comprises a specific crystalline aluminosilicate or molecular sieve. Particular crystalline aluminosilicates include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecule as, for instance, when smaller normal paraffin molecules are separated from larger isoparaffin molecules by using a particular molecular sieve. In the process of this invention, however, the term "molecular sieves" although widely used is not strictly suitable since the separation of specific C8 aromatic isomers is dependent on differences in electrochemical attraction of the different isomers and the adsorbent rather than on pure physical size differences in the isomer molecules.

In hydrated form, the crystalline aluminosilicates generally encompass those zeolites represented by the Formula 1 below:

Formula 1

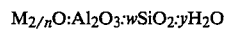

$$M_{2/n}O:Al_2O_3:wSiO_2:yH_2O$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The cation "M" may be one or more of a number of possible cations.

The prior art has generally recognized that adsorbents comprising the type X structured and the type Y structured zeolites can be used in certain adsorptive separation processes. These zeolites are described and defined in U.S. Pat. Nos. 2,882,244 and 3,120,007, respectively, incorporated herein by reference. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in Formula 2 below:

Formula 2

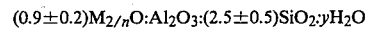

$$(0.9 \pm 0.2)M_{2/n}O:Al_2O_3:(2.5 \pm 0.5)SiO_2:yH_2O$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio is $2.5 \pm 0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is therefore referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 3 below:

Formula 3

$(0.9 \pm 0.2)M_{2/n}O:Al_2O_3 \cdot wSiO_2 \cdot yH_2O$ where "M" is at least one cation having a valence not more than 3, "n" represents the valence of "M", "w" is a value greater than about 3 up to about 8, and "y" is a value up to about 9 depending upon the identity of "M", and the degree of hydration of the crystal. The $SiO_2/Al_2O_3$ mole ratio for type Y structured zeolites can thus be from about 3 to about 8. Like the type X structured zeolite, the cation "M" may be one or more of a variety of cations but, as the type Y zeolite is initially prepared, the cation "M" is also usually predominately sodium. The type Y zeolite containing predominantely sodium cations at the exchangeable cationic sites is therefore referred to as a sodium-type Y zeolite.

Cations occupying exchangeable cationic sites in the zeolite may be replaced with other cations by ion exchange methods generally known to those having ordinary skill in the field of crystalline aluminosilicates. Such methods are generally performed by contacting the zeolite with an aqueous solution of the soluble salt of the cation or cations desired to be placed upon the zeolite. After the desired degree of exchange takes place, the sieves are removed from the aqueous solution, washed, and dried to a desired water content. By such methods the sodium cations and any non-sodium cations which might be occupying exchangeable sites as impurities in a sodium-type X or sodium-type Y zeolite can be partially or essentially completely replaced with other cations.

For the particular separation process of this invention where meta-xylene is to be recovered in high purity as an extract component, it is necessary that the zeolite adsorbent possess selectivity for meta-xylene with respect to ethylbenzene and the other xylene isomers so that everything other than meta-xylene will be rejected rather than adsorbed by the adsorbent. While separation is theoretically possible when the selectivity of meta-xylene with respect to ethylbenzene and the other xylene isomers is greater than 1, it is preferred that such selectivity be near to 2. Like relative volatility, the higher the selectivity, the easier the separation is to perform. Higher selectivities permit a smaller amount of adsorbent to be used. To separate meta-xylene in high purity and at high recoveries, it is also necessary that the adsorbent possess high selectivity for the meta-xylene with respect to the desired desorbent material. Toluene has been found to be the ideal desorbent material for this process.

It has been found that for the process of this invention adsorbent comprising Y zeolites containing sodium at the exchangeable cationic sites and having a silica to alumina mole ratio of from about 4.5 to about 5.0 satisfy these selectivity requirements and the other adsorbent requirements previously discussed. The adsorbent for this process will typically comprise the above Y zeolite in concentrations generally ranging from about 75 wt. % to about 98 wt. % of the adsorbent based on a volatile free composition. The remaining material in the adsorbent will generally comprise amorphous silica or alumina or both present in intimate mixture with the zeolite material to aid in forming the zeolite into particles of the desired size. This amorphous material may be an adjunct of the manufacturing process of the type Y zeolite (for example, intentionally incomplete purification of the zeolite during its manufacture) or it may be added to the relatively pure zeolite to aid in forming the zeolite into such particles as extrudates, aggregates, tablets, pills or macrospheres. The adsorbent for this process will preferably be smaller particles in about 20 to 40 U.S. mesh particle size range which can be produced by grinding and screening the larger aforementioned particles.

EXAMPLE 1

This example sets forth data acquired from the previously described pulse test apparatus when using various adsorbents and feed pulses comprising a mixture of ethylbenzene and the xylene isomers. The adsorbent comprises zeolites of different exchangeable cations, but all with silica to alumina mole ratios ($SiO_2/Al_2O_3$) within the range of about 4.5 to about 5.0. The process temperature was 150° C. and the pressure was 100 psig to maintain liquid-phase operations. The tracer used was n-nonane. The desorbent used was pure toluene. Following is the data obtained:

| Adsorbent | Relative Selectivities | | | | | |
| --- | --- | --- | --- | --- | --- | --- |
| | Ca-X | Sr-X | Na-X | Na-Y | Li-Y | Li-X |
| m-xyl/etbenz | 3.90 | 3.18 | 1.20 | 3.94 | 2.99 | 1.05 |
| m-xyl/p-xyl | 1.77 | 1.35 | 1.00 | 1.90 | 1.78 | 1.11 |
| m-xyl/o-xyl | 1.20 | 1.35 | 1.08 | 1.88 | 1.38 | 0.74 |

The above data illustrates that it is only the Na-Y zeolite that exhibits sufficiently high relative selectivity for meta-xylene as compared to ethylbenzene and each of the other xylene isomers to enable an efficient separation of the meta-xylene from a mixture of all of the $C_8$ aromatics.

EXAMPLE 2

In order to determine the effect of the silica to alumina mole ratio in the Na-Y zeolite on the above relative selectivities, a pulse test was repeated using a Na-Y zeolite having a silica to alumina mole ratio of 3.7. Following are the results, including a comparison with the Na-Y zeolite of Example 1 for which the $SiO_2/Al_2O_3$ was 4.9:

| Zeolite Type | Relative Selectivities | |
| --- | --- | --- |
| | Na-Y | |
| $SiO_2/Al_2O_3$ | 4.9 | 3.7 |
| m-xyl/etbenz | 3.94 | 2.08 |
| m-xyl/p-xyl | 1.90 | 1.39 |
| m-xyl/o-xyl | 1.88 | 1.07 |

The above thus illustrates the criticality of the silica to alumina ratio for the zeolite to be effective in meta-xylene separation. The meta-xylene relative selectivities for the Na-Y zeolite having a $SiO_2/Al_2O_3$ of 3.7 would be wholly inadequate for an efficient separation, particularly with regard to para-xylene and orthoxylene.

EXAMPLE 3

This example presents data obtained through the practice of this invention using the hereinbefore described carousel test unit. The adsorbent was a Na-Y zeolite with a silica to alumina mole ratio of 4.9. Toluene was the desorbent and the feed had the following composition:

paraffins: 6.0%
    ethylbezene: 27.0%
    p-xylene: 17.8%
    m-xylene: 45.1%
    o-xylene: 4.1%

Process conditions were a temperature of 150° C., a pressure of 100 psig, a rotary valve cycle time of 1 hour and an A/F ratio (adsorbate to feed ratio) of 1.5.

A meta-xylene purity of 99.5+% at a yield of greater than 98% was obtained, thus illustrating the effectiveness and efficiency of the invention.

I claim as my invention:

1. A process for separating meta-xylene from a feed mixture comprising meta-xylene the other xylene isomers and ethylbenzene which process comprises contacting at adsorption conditions said mixture with an adsorbent comprising a type Y zeolite containing sodium at the exchangeable cationic sites and having a silica to alumina mole ratio of from about 4.5 to about 5.0, selectively adsorbing therein said meta-xylene to the substantial exclusion of the remaining components of said mixture and thereafter recovering high-purity meta-xylene.

2. The process of claim 1 including the step of treating the adsorbent containing said meta-xylene with a desorbent material comprising toluene to remove said meta-xylene therefrom as a fluid extract stream.

3. The process of claim 1 further characterized in that said adsorption conditions include a temperature within the range of from about 20° C. to about 250° C. and at a pressure within the range of from about atmospheric to about 500 psig.

4. The process of claim 3 further characterized in being effected in the liquid phase.

5. A process for separating meta-xylene from a feed mixture comprising the xylene isomers and ethylbenzene which process employs an adsorbent comprising a type Y zeolite containing sodium at the exchangeable cationic sites and having a silica to alumina mole ratio of from about 4.5 to about 5.0 and which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at adsorption conditions to effect the selective adsorption of said meta-xylene to the substantial exclusion of the remaining components of said mixture by said adsorbent in said adsorption zone and withdrawing a raffinate output stream comprising said remaining components from said adsorption zone;

(f) passing a desorbent material having an average boiling point substantially different from that of the feed mixture into said desorption zone at desorption conditions to effect the displacement of said meta-xylene from the adsorbent in said desorption zone;

(g) withdrawing an extract output stream comprising said remaining components from said desorption zone; and (h) periodically advancing through said column of adsorbent in a downstream direction with respect to fluid flow in said adsorption zone said feed input stream, a raffinate output stream, desorbent input stream, and extract output stream to effect the shifting of zones through said adsorbent and the production of said extract output and raffinate output streams.

6. The process of claim 5 further characterized in that said desorbent material comprises toluene.

7. The process of claim 5 further characterized in that said adsorption conditions and said desorption conditions include a temperature within the range of from about 20° C. to about 250° C. and a pressure within the range of from about atmospheric to about 500 psig.

8. The process of claim 7 further characterized in being effected in the liquid phase.

9. The process of claim 5 further characterized in that said raffinate output stream contains desorbent material.

10. The process of claim 5 further characterized in that said extract output stream contains desorbent material.

11. The process of claim 5 further characterized in that it includes the step of maintaining a buffer zone immediately upstream from said desorption zone, said buffer zone defined as the adsorbent located between said desorbent input stream at a downstream boundary of said buffer zone and said raffinate output stream at an upstream boundary of said buffer zone.

* * * * *